(12) United States Patent
Ramgopal et al.

(10) Patent No.: US 7,622,602 B2
(45) Date of Patent: Nov. 24, 2009

(54) METHOD FOR PREPARING A DIALKYL CARBONATE, AND ITS USE IN THE PREPARATION OF DIARYL CARBONATES AND POLYCARBONATES

(75) Inventors: Thodla Ramgopal, Karnataka (IN); Mario Perez Collado, Cartagena (ES); Vijaya Kumar Narasaiah, Karnataka (IN); Ignacio Vic Fernandez, Murcia (ES)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 532 days.

(21) Appl. No.: 11/248,390

(22) Filed: Oct. 12, 2005

(65) Prior Publication Data

US 2007/0083059 A1 Apr. 12, 2007

(51) Int. Cl.
*C07C 69/96* (2006.01)
(52) U.S. Cl. .................................................. 558/277
(58) Field of Classification Search .................. 558/277
See application file for complete search history.

(56) References Cited

U.S. PATENT DOCUMENTS

| | | | |
|---|---|---|---|
| 3,153,008 A | 10/1964 | Fox et al. ...................... 260/47 |
| 4,182,726 A | 1/1980 | Illuminati et al. ........... 260/463 |
| 4,218,391 A | 8/1980 | Romano et al. ............. 260/463 |
| 4,318,862 A | 3/1982 | Romano et al. ............. 260/463 |
| 4,360,659 A | 11/1982 | Sikdar ........................ 528/196 |
| 5,220,782 A | 6/1993 | Brown et al. |
| 5,527,943 A | 6/1996 | Rivetti et al. ................ 528/277 |
| 5,536,864 A | 7/1996 | Paret et al. |
| 5,550,278 A | 8/1996 | Rechner et al. |
| 5,686,644 A | 11/1997 | Rivetti et al. ................ 528/277 |
| 6,458,914 B2* | 10/2002 | Kimura et al. .............. 528/196 |
| 2003/0055199 A1 | 3/2003 | Boden et al. |
| 2003/0060650 A1* | 3/2003 | Boden et al. ................ 558/277 |
| 2003/0092872 A1 | 5/2003 | Boden et al. |
| 2003/0153782 A1* | 8/2003 | Boden et al. ................ 558/277 |
| 2003/0236428 A1* | 12/2003 | de Broek et al. ............ 558/277 |

FOREIGN PATENT DOCUMENTS

| | | |
|---|---|---|
| EP | 0634390 | 1/1995 |
| EP | 0685453 | 12/1995 |
| EP | 0460732 A1 | 12/1999 |

OTHER PUBLICATIONS

International Search Report for International Application No. PCT/US2006/039456; mailed Feb. 22, 2007; 5 pages.
Written Opinion of the International Searching Authority for International Application No. PCT/US2006/039456; mailed Feb. 22, 2007; 5 pages.
Pacheco, et al. "Review of Dimethyl Carbonate (DMC) Manufacture and Its Characteristics as a Fuel Additive" Energy and Fuels, vol. 11, No. 1, 1997, pp. 2-29.

* cited by examiner

*Primary Examiner*—Golam M. M. Shameem
*Assistant Examiner*—Susannah Chung

(57) ABSTRACT

A method of making a dialkyl carbonate comprises: reacting, in a reactor comprising tantalum, an alkanol, oxygen, and carbon monoxide, in the presence of a catalyst. The reaction occurs in a mixture comprising a liquid phase wherein the liquid phase comprises about 4 to about 12 weight percent water based on the total weight of the liquid phase.

8 Claims, 6 Drawing Sheets

METHOD FOR PREPARING A DIALKYL CARBONATE, AND ITS USE IN THE PREPARATION OF DIARYL CARBONATES AND POLYCARBONATES

BACKGROUND OF INVENTION

Polycarbonate resins are useful materials valued for their physical and optical properties. Methods for the preparation of polycarbonate resins include interfacial processes and melt processes. In interfacial processes, as described, for example, in U.S. Pat. No. 4,360,659 to Sikdar, a bisphenol is reacted with phosgene in the presence of solvents. In melt processes, as described, for example, in U.S. Pat. No. 3,153,008 to Fox, a bisphenol is reacted with a diaryl carbonate. Melt processes are advantageous because they avoid the use of phosgene and solvents.

Use of a melt process for polycarbonate synthesis requires an industrially efficient process for producing diaryl carbonates. There are several known processes for producing diaryl carbonates. One example of such a process is described by U.S. Pat. No. 4,182,726 to Illuminati et al. In this process, diaryl carbonates are produced by reacting dialkyl carbonates with a phenol in the presence of a catalyst such as $AlCl_3$.

U.S. Pat. No. 4,182,726 also demonstrates that diaryl carbonates can be reacted together with dihydric phenols to produce polycarbonates (see Scheme I, below).

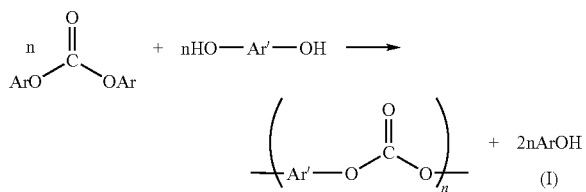

A preferred process for making dialkyl carbonates is illustrated in Scheme II, below, and described, for example, in U.S. Pat. Nos. 5,527,943 to Rivetti et al.; and 4,218,391 and 4,318,862 to Romano et al.

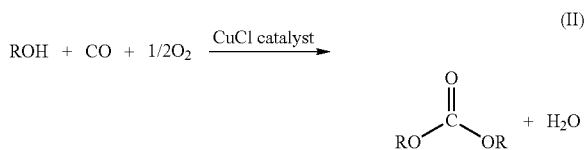

As can be seen in Scheme (II) the reaction produces water as a by-product. Also, hydrochloric acid (HCl) may be continuously added to the reaction mixture to maintain a desired molar ratio of chloride to copper. Therefore, HCl, CuCl catalyst, and water are typically found in the stream exiting the reactor vessel. Hydrochloric acid and copper chlorides are very corrosive in the presence of water, so equipment made from corrosion-resistant materials, such as glass-lined or tantalum vessels, must be used in the reaction section of a chemical plant making dialkyl carbonates by this process. However, even corrosion resistant materials can suffer deterioration over time.

Accordingly, there is therefore a need for a dialkyl carbonate process that reduces the amount of corrosion.

BRIEF DESCRIPTION OF THE INVENTION

The above-described and other drawbacks and disadvantages of the prior art are alleviated by a method of making a dialkyl carbonate comprising: reacting, in a reactor comprising tantalum, an alkanol, oxygen, and carbon monoxide, in the presence of a catalyst comprising copper. The reaction occurs in a mixture comprising a liquid phase wherein the liquid phase comprises about 4 to about 12 weight percent water based on the total weight of the liquid phase.

The method is described in greater detail below.

DETAILED DESCRIPTION

Figure 1:
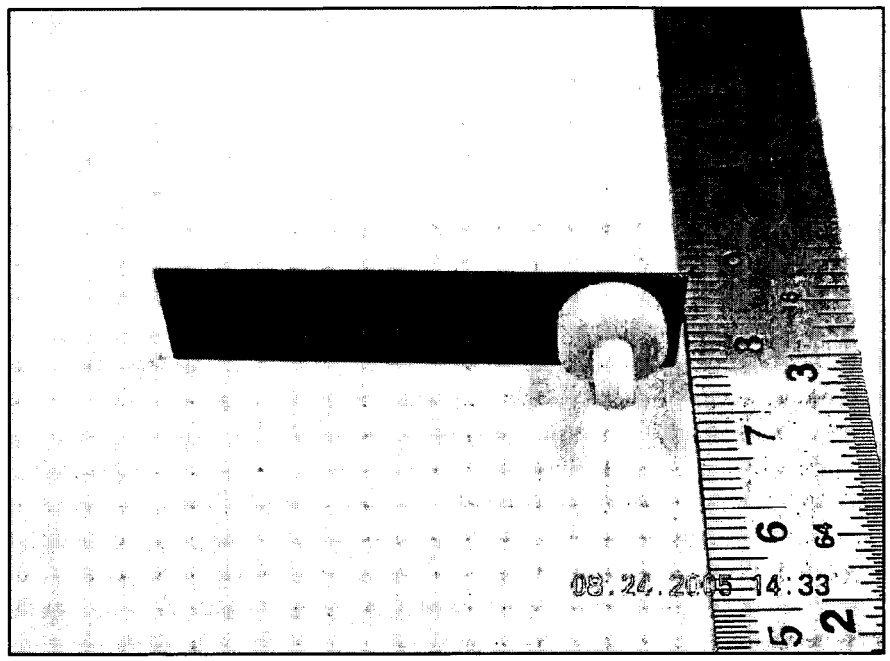
FIG. 1 is a picture of a creviced sample.

The modifier "about" used in connection with a quantity is inclusive of the stated value and has the meaning dictated by the context (e.g., includes the degree of error associated with measurement of the particular quantity).

All ranges disclosed herein are inclusive and combinable (e.g., ranges of "up to about 25 wt %, with about 5 wt % to about 20 wt % desired," is inclusive of the endpoints and all intermediate values of the ranges of "about 5 wt % to about 25 wt %," etc.).

It has been discovered that dialkyl carbonate synthesis can result in the corrosion of tantalum and tantalum alloys employed in the reactor. Surprisingly the presence of a sufficient amount of water is important for decreasing and even preventing corrosion of reactor components comprising tantalum or tantalum alloy such as an inner surface. Maintaining a particular water level in the reaction, particularly in amounts greater than or equal to about 4 weight percent, is counter intuitive as water is a product of the reaction and thus its presence would be expected to slow or stop the reaction. Despite maintaining the water level above 4 weight percent the reaction proceeds with excellent yield.

One embodiment is a method of making a dialkyl carbonate comprising: reacting, in a reactor comprising tantalum, an alkanol, oxygen, carbon monoxide, and a catalyst comprising copper. The reaction occurs in a mixture comprising a liquid phase wherein the liquid phase comprises about 4 to about 12 weight percent water based on the total weight of the liquid phase. In one embodiment the amount of water in the liquid phase can be about 5 to about 8 weight percent, or, more specifically, about 6 to about 8 weight percent. The presence of the water decreases corrosion of the tantalum lining of the reactor.

The reaction produces dialkyl carbonate and water. Additionally alkyl chloroformate and carbon dioxide may be produced. Hydrochloric acid may also be present. The dialkyl carbonate is isolated from the resulting mixture.

In one embodiment the amount of dialkyl carbonate present in the reaction mixture is about 38 weight percent to about 52 weight percent, based on the total weight of the liquid phase of the reaction mixture. Within this range the amount of dialkyl carbonate can be greater than or equal to 40 weight percent. Also within this range the amount of dialkyl carbonate can be less than or equal to 50 weight percent.

Suitable alkanols include primary, secondary, and tertiary $C_1$-$C_4$ alkanols, such as methanol, ethanol, n-propanol, isopropanol, n-butanol, isobutanol, and combinations of two or more of the foregoing alkanols. In one embodiment, the alkanol is methanol.

Oxygen may be provided in any form, with gaseous forms being preferred. Suitable oxygen sources include, for example, air, and oxygen-containing gases having greater than or equal to about 95 weight percent molecular oxygen, or, more specifically, greater than or equal to about 99 weight percent molecular oxygen. Suitable oxygen-containing gases are commercially available from, for example, Air Products.

Carbon monoxide can be supplied as a gas having greater than or equal about 70 weight percent, or, more specifically, greater than or equal to about 90 weight percent, or, even more specifically, greater than or equal to about 99 weight percent, carbon monoxide. Suitable carbon monoxide-containing gases are commercially available from, for example, Air Products.

The catalyst may comprise an oxidizing metal in combination with a halide such as ferrous chloride, cobalt chloride, cuprous chloride, cupric chloride, or a combination of two or more of the foregoing metal halides. In one embodiment, the catalyst comprises copper. In one embodiment the catalyst comprises copper and chloride ion in a molar ratio of about 0.5 to about 1.5. Within this range, a molar ratio can be greater than or equal to 0.8. Also within this range, a molar ratio can be less than or equal to 1.3. Exemplary catalysts include cuprous chloride (CuCl) and cupric chloride ($CuCl_2$). In one embodiment the catalyst comprises cuprous chloride. During operation of the process, a suitable chloride ion concentration may be maintained by the addition of hydrochloric acid (HCl).

The corrosion of the reaction components comprising tantalum can be affected by the repassivation potential and the corrosion potential of the reaction mixture. Importantly, the difference between the repassivation potential of the mixture in the reactor and the corrosion potential of the mixture in the reactor is greater than 0 millivolts (mV) to mitigate localized corrosion. Otherwise expressed: repassivation potential–corrosion potential>0 millivolts (mv). In one embodiment, repassivation potential–corrosion potential=200 mV to 500 mV. Within this range, repassivation potential–corrosion potential can be greater than or equal to 250 mV, or, more specifically, greater than or equal to 300 mV. Repassivation potential and corrosion potential may be determined as explained in the examples below.

The catalyzed reaction of alkanol, oxygen, and carbon monoxide may be performed in a single reactor or in two or more reactors. The conditions for performing this step should be selected to maximize the yield of dialkyl carbonate while minimizing the degradation of dialkyl carbonate and corrosion of the reactor. In one embodiment the reaction is performed in a single reactor, at a temperature of about 50° C. to about 250° C. Within this range, the temperature can be greater than or equal to about 100° C. Also within this range, the temperature can be less than or equal to about 150° C. The reactor is typically kept at a pressure of about 15 to about 35 kilograms per square centimeter ($kg/cm^2$) above atmospheric pressure. Within this range, the pressure can be greater than or equal to about 20 $kg/cm^2$ above atmospheric pressure. Also within this range, the pressure can be less than or equal to about 28 $kg/cm^2$ above atmospheric pressure. In the case of dual reactor systems, the catalyst may be recycled between tanks. The catalyst concentration should be sufficiently high to produce an acceptable yield, but should be kept below a concentration that would cause solid settling of the catalyst in the reactor or clogging of the equipment. The reactants alkanol, oxygen, and carbon monoxide are preferably added in a molar ratio of (about 0.5 to about 0.7):(about 0.04 to about 0.06):(about 0.8 to about 1.2), respectively. In one embodiment the molar ratio of alkanol:oxygen:carbon monoxide is (about 0.6):(about 0.05):(about 1).

The amount of catalyst used relative to the reactants will depend on the identity of the catalyst. For example, when the catalyst comprises CuCl, the catalyst concentration is about 140 to about 180 grams per liter of reaction mixture. During operation, the catalyst may initially be added from a catalyst tank. Sufficient HCl is preferably added to the reactor from a hydrochloric acid tank during the course of the reaction to maintain a molar ratio of Cu:Cl close to 1.0. The HCl in the hydrochloric acid tank may be either dilute or concentrated. The concentration of HCl may be continuously determined and controlled by the addition of HCl. A typical mass ratio for HCl feed to total liquid feed is about $1.1 \times 10^{-2}$ to $2 \times 10^{-2}$ kilogram HCl feed/kilogram of liquid feed, from design mass balance. In one embodiment, the HCl is added as dilute HCl having a concentration of 20% weight/weight to 30% weight/weight.

The alkanol, catalyst, and HCl may be fed in combination or separately. In one embodiment, HCl is fed to the reactor separately from the alkanol, catalyst or combination of alkanol and catalyst.

The reaction produces a mixture comprising a dialkyl carbonate, an alkyl chloroformate, hydrochloric acid, water, carbon dioxide, and carbon monoxide. The mixture may further comprise residual alkanol and oxygen, as well as side-products such as alkyl chlorides and dialkyl ethers. The mixture is typically withdrawn from the reactor in a gas/vapor form. The term "vapor" is meant to refer to gaseous organic components of the mixture such as, for example, evaporated dialkyl carbonates, alcohols, alkyl chloroformates, etc., and to water vapor. That is, the term "vapor" refers to fluids having a boiling point of at least −50° C. at one atmosphere. In contrast, the term "gas" is meant to refer to the gaseous oxygen, carbon dioxide, carbon monoxide, and optional nitrogen. That is, the term "gas" refers to fluids having a boiling point less than −50° C. at one atmosphere. The vapor may be at least partially condensed in a condenser, and fed to one or more gas-liquid separators. In one embodiment, substantially all of the gas is removed from the mixture. It is preferred that the vapor in the mixture be in a partially condensed form (i.e., greater than or equal to about 10% condensed), or, more specifically, a fully condensed form (i.e., greater than or equal to about 90% condensed), before entering the gas-liquid separator.

The mixture exiting the gas-liquid separator may be in a single liquid phase. After the gas-liquid separator, the mixture may proceed through a fluid passageway that removes alkyl chloroformate from the mixture. It will be understood that the terms "remove" and "removal" in reference to a particular chemical species encompass any chemical or physical process that reduces the concentration of the species in the mixture. The alkyl chloroformate may be removed from the condensate by any method such as heating, increasing pressure, increasing residence time, adding a polar solvent, adsorbing, separating with a membrane (including gas and liquid membrane separation), pervaporating, passing through an ion exchange resin, exposing to a stoichiometric reagent, exposing to a catalytic reagent, and the like, and combinations comprising at least one of the foregoing techniques. In a one embodiment, the alkyl chloroformate is removed from mixture by reaction with water (see Scheme III) or alkanol (see Scheme IV).

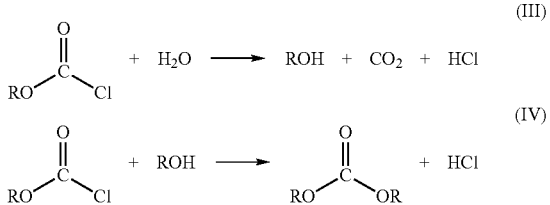

The condensate may also be corrosive to the equipment after the gas-liquid separator. In one embodiment the water concentration of the condensate is maintained at a level greater than or equal to 4 weight percent, based on the total weight of the condensate. The condensate may comprise water in an amount up to, and including, about 12 weight percent. Once corrosion producing elements, such as the catalyst components, hydrochloric acid and reaction side products such as alkyl chloroformate, are removed the water concentration can be reduced to below 4 weight percent. Catalyst components and hydrochloric acid can be removed by any method known in the art, such as an acid removal column, as long as the method does not substantially degrade the dialkyl carbonate.

The dialkyl carbonate may then be purified by methods known in the art such as decantation (phase separation), distillation and combinations of decantation and distillation.

The method of making dialkyl carbonate may be operated, for example, in a batch, semi-batch, or continuous manner.

Dialkyl carbonates prepared according to the method are useful for the preparation of diaryl carbonates. For example, diaryl carbonates may be generated by the reaction of a dialkyl carbonate with a phenol in the presence of a catalyst or by the reaction of a dialkyl carbonate with an aromatic alcohol in the presence of a transesterification catalyst. Exemplary transesterification catalysts include titanium compounds like titaniumtetraphenoxide (Ti(OPh)$_4$), and titaniumtetrachloride, organotin compounds, and compounds of copper, lead, zinc, iron, and zirconium.

The diaryl carbonate may in turn be reacted with a dihydroxy compound in melt to form a polycarbonate (see Scheme I, above).

Some illustrative, non-limiting examples of suitable dihydroxy compounds include the following: resorcinol, 4-bromoresorcinol, hydroquinone, methyl hydroquinone, 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl) cyclopentane, 1,1-bis(4-hydroxyphenyl)cyclohexane, 1,1-bis(4-hydroxyphenyl)isobutene, 1,1-bis(4-hydroxyphenyl) cyclododecane, trans-2,3-bis(4-hydroxyphenyl)-2-butene, 2,2-bis(4-hydroxyphenyl)adamantine, (alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl) propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, and the like, as well as combinations comprising at least one of the foregoing dihydroxy compounds.

Specific examples of bisphenol compounds include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-1-methylphenyl) propane, 1,1-bis(4-hydroxy-t-butylphenyl) propane, 3,3-bis(4-hydroxyphenyl) phthalimidine, 2-phenyl-3,3-bis(4-hydroxyphenyl) phthalimidine (PPPBP), and 1,1-bis(4-hydroxy-3-methylphenyl)cyclohexane (DMBPC). Combinations comprising at least one of the foregoing dihydroxy compounds may also be used.

In one embodiment, dimethyl carbonate prepared according to the method described herein may be reacted with phenoxide or phenol to form diphenyl carbonate, which in turn may be reacted with an aromatic dihydroxy compound such as bisphenol A to form a polycarbonate.

The invention is further illustrated by the following non-limiting examples.

EXAMPLES

Polarization scans were performed using a potentiostat and an electrochemical cell to determine the repassivation potential. The electrochemical cell consisted of a working electrode (WE), reference electrode (RE) and counter electrode (CE). The electrochemical cell was maintained at a temperature of 132° C. and a pressure of 24 bar (2.4 Megapascals (MPa)).

The working electrodes were 50 millimeters (mm) X 2 mm rectangular tantalum-2.5 tungsten alloy (Ta-2.5 W) specimens having a thickness of 0.5 mm that were polished using 120 grit silicone carbide (SiC) paper. Some samples had welds and some were creviced. Samples of welded Ta-2.5 W were prepared by welding two sheets of Ta-2.5 W together. The samples were cut up such that the weld portion was immersed in the liquid. The creviced samples were prepared by using a Teflon™ nut and washer to create a crevice as shown in FIG. 1. The samples were spot welded to a tantalum wire which was fitted through a high pressure connax fitting such that half the length of the specimen was immersed.

The counter electrode was platinum. The reference electrode was a Ag/AgCl electrode. The electrolyte for the reference electrode was 99 weight (wt %) methanol, 1 wt % water containing 0.1 molar lithium chloride.

Figure 2:
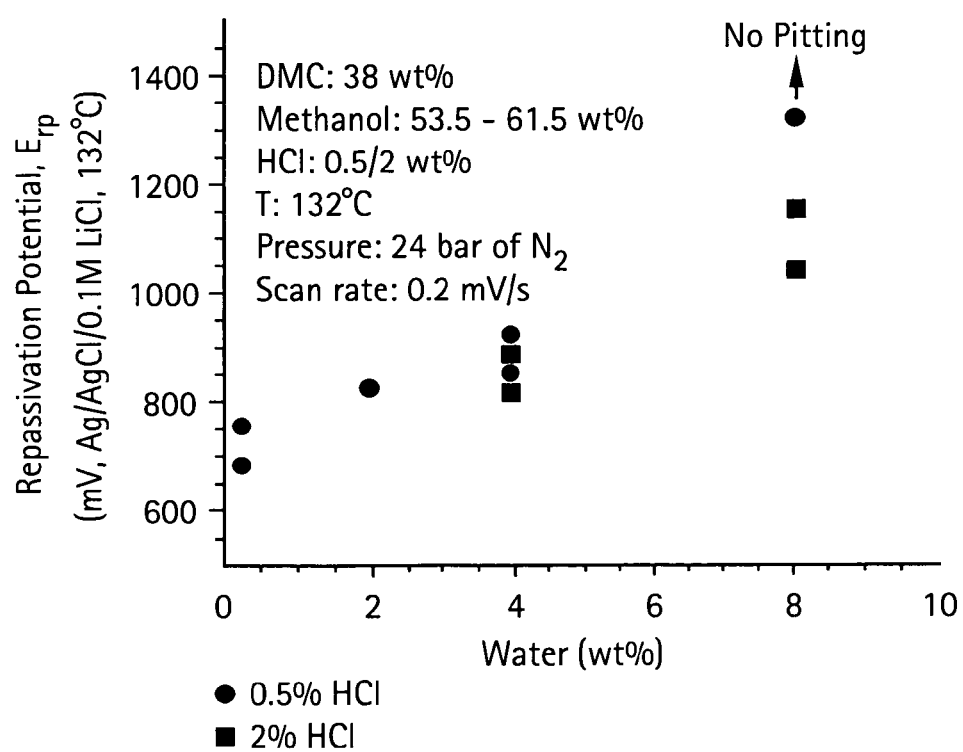
FIG. 2 is a graph of repassivation potential at various water and HCl concentrations.
Figure 3:
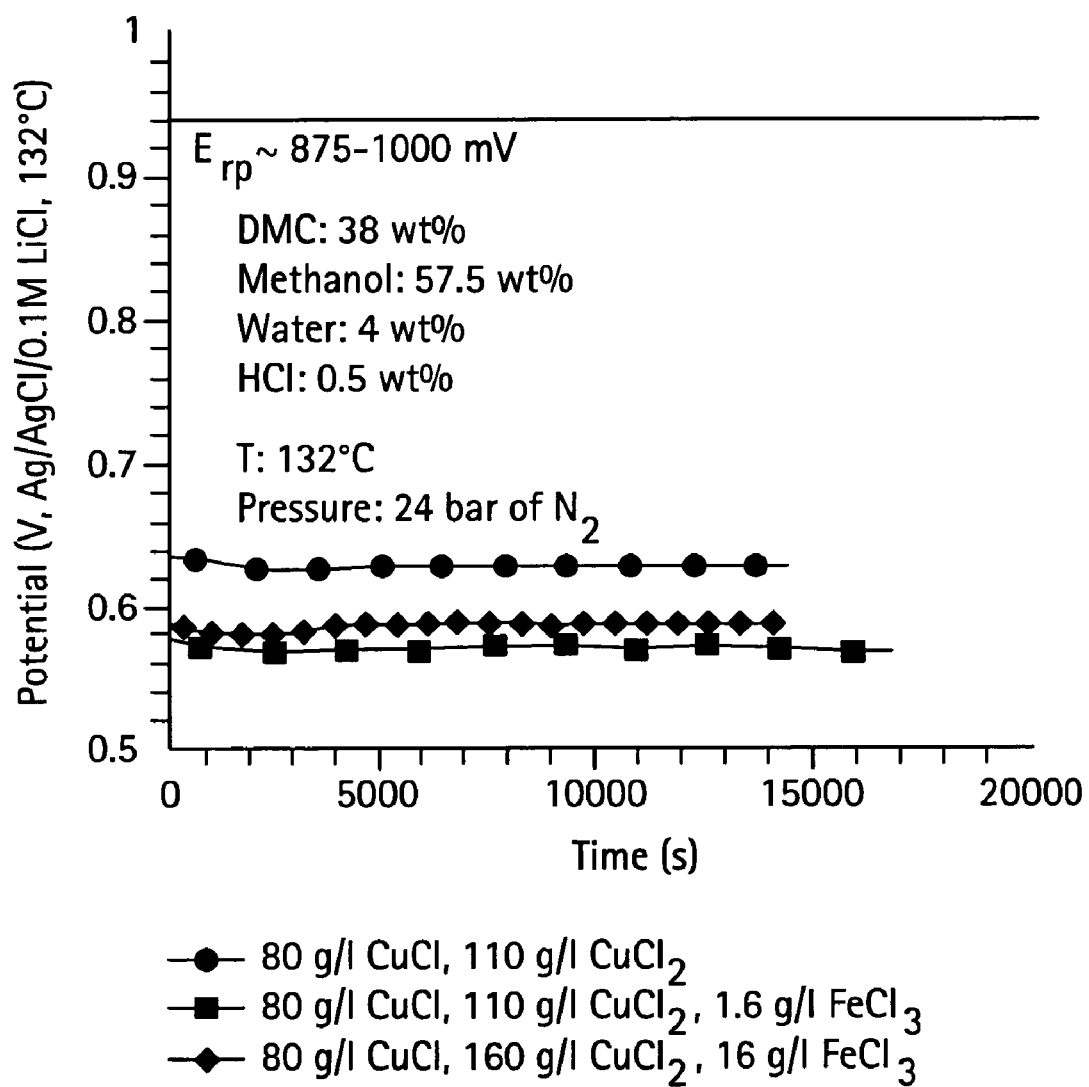
FIGS. 3-6 are graphs showing corrosion potential measurement for various combinations of water and HCl concentrations.
Figure 4:
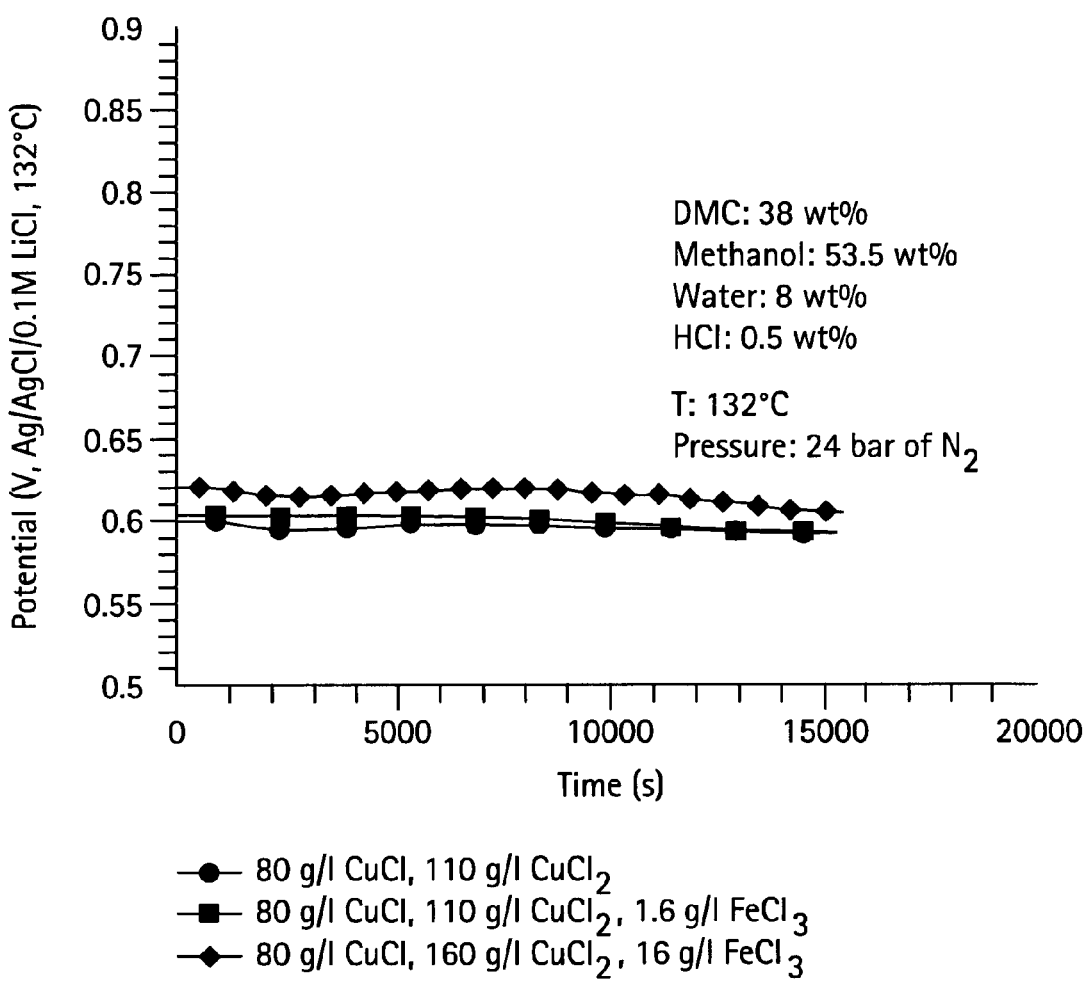
Figure 5:
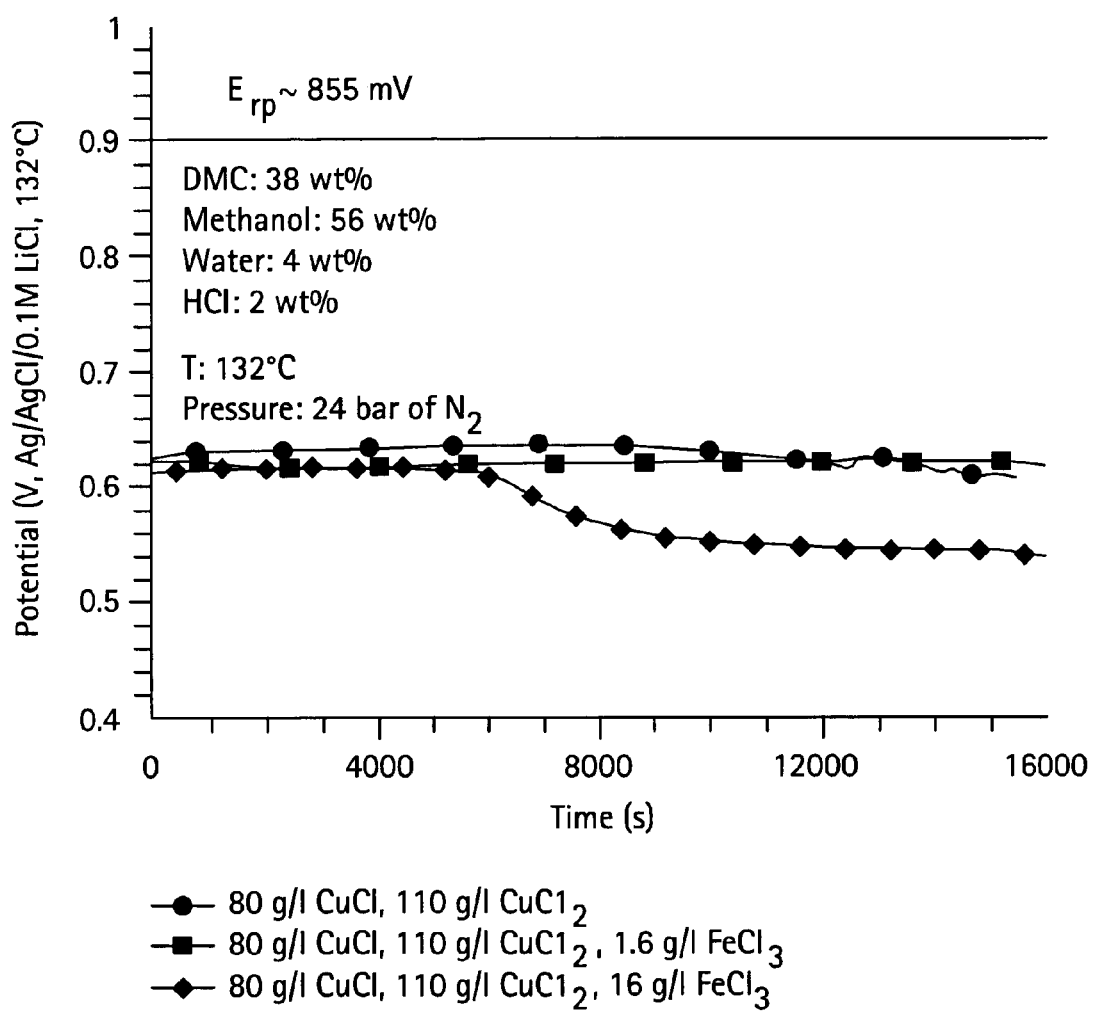
Figure 6:
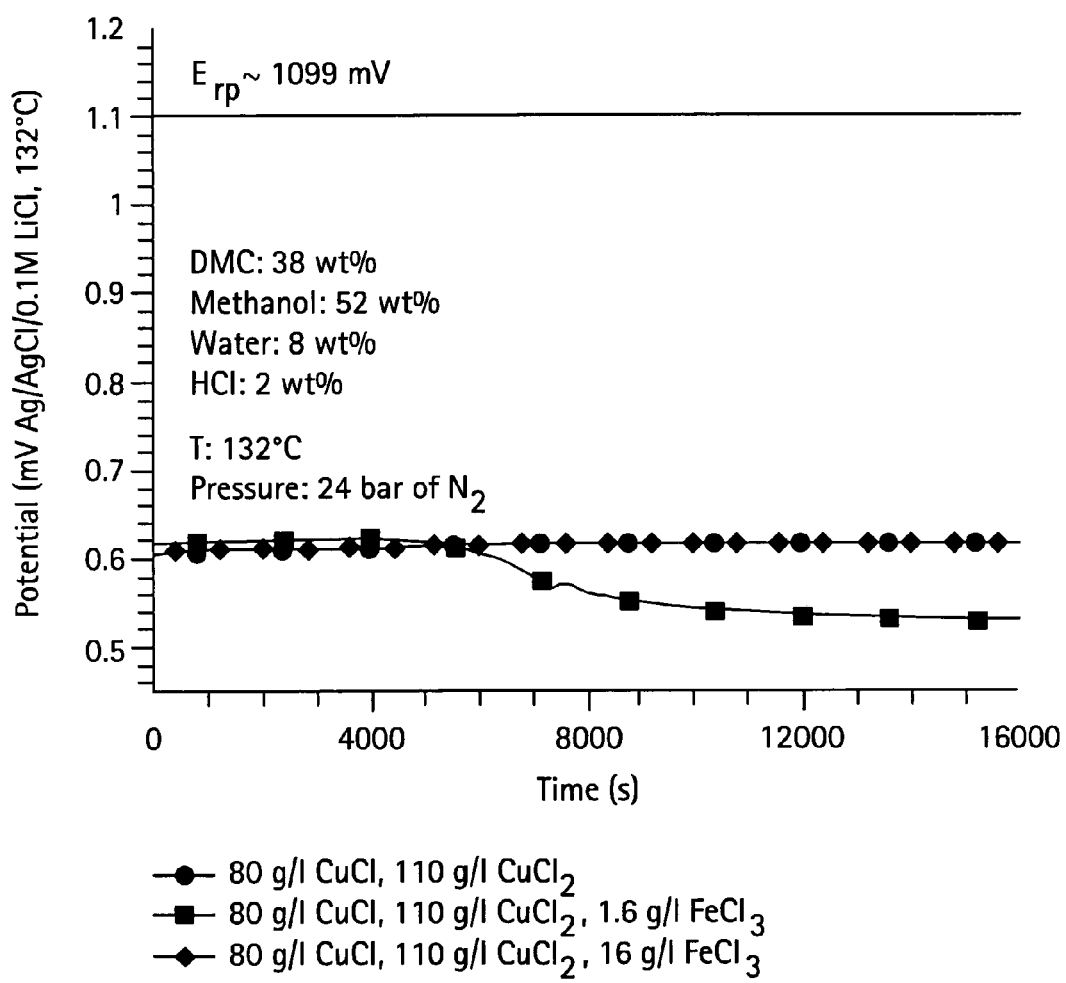

The electrolyte used in the electrochemical cell simulated the mixture present in a reaction to make dialkyl carbonate. The catalyst was not present because polarization in environments containing strong oxidizers would result in a combination of plating of redox species and metal dissolution reactions. The concentration of water was varied as shown in FIG. 1. Polarization scans were performed at 0.2 millivolt per second (mV/s) after an open circuit potential (OCP) delay of 3600 seconds. The potential was scanned in the forward direction up to 2.5 volts (V) and then reversed to −0.1 V below the OCP. Two sets of scans were performed under all conditions. Results are shown in FIG. 2. Hydrochloric acid (HCl), water, and dimethyl carbonate (DMC) amounts are in weight percent based on the total weight of the entire solution. Methanol made up the balance of the solution.

FIG. 2 shows that the repassivation potential increases significantly as the water content increases. Analysis was performed at two different HCl concentrations. The repassivation potential is a measure of the tantalum alloy's susceptibility to corrosion. When the repassivation potential is high, resistance to corrosion is improved.

Corrosion potential measurements were performed using the same electrochemical cell set up. Corrosion potential measurements were made for a duration of 4 hours. The electrochemical cell electrolyte included a combination of copper chloride and copper dichloride, or copper chloride, copper dichloride and iron trichloride. Duplicate samples were tested. Samples were immersed in solution and the corrosion potential was measured. The amounts of HCl, water and metal chlorides were varied. The amount of DMC was held constant at 38 weight percent, based on the total weight of the solution. Methanol made up the balance of the solution. Representative results are shown in FIGS. 3-6. A representative repassivation potential, $E_{rp}$, is shown in some figures for comparison. Corrosion potential measurements made using welded and creviced samples exhibited similar values.

Figure 7:
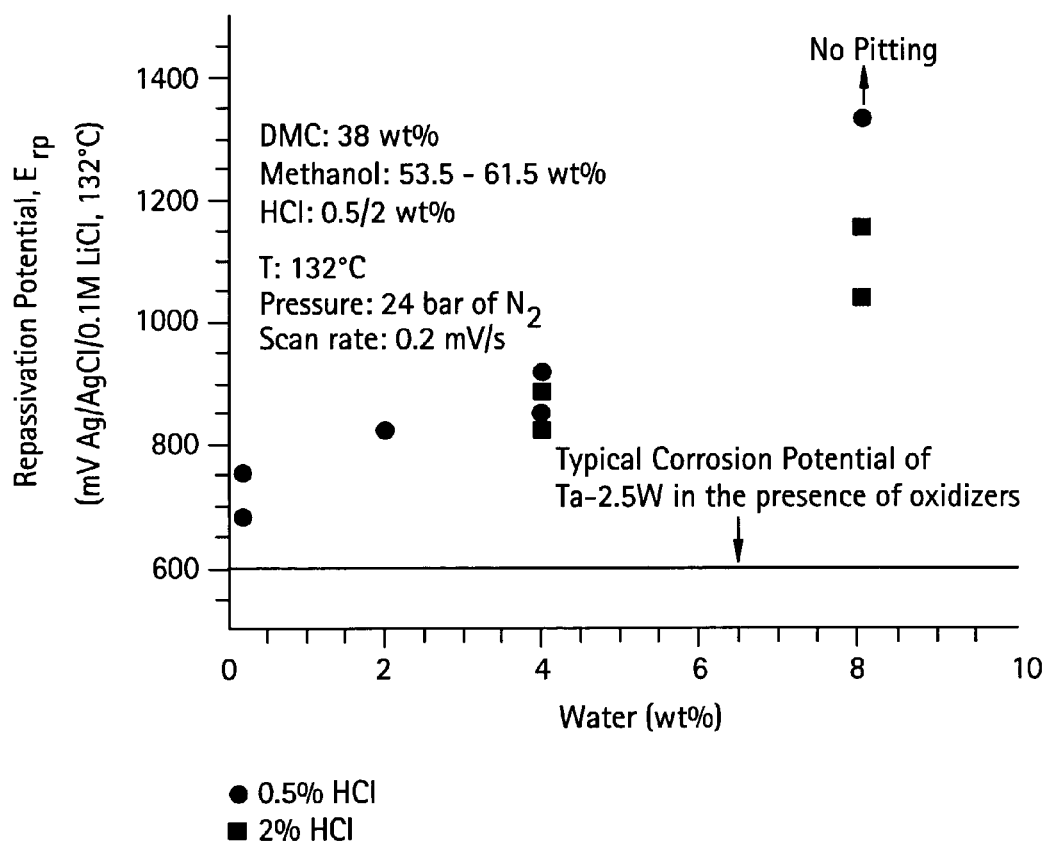
FIG. 7 is a graph comparing repassivation potential to corrosion potential.

FIG. 7 is a graph comparing a representative corrosion potential to various repassivation potentials. As can be seen from FIGS. 2-6 and FIG. 7, in particular, increasing amounts of water present in the solution results in an increasing difference between the repassivation potential and the corrosion potential. As a result the incidence of tantalum corrosion decreased. In some cases, corrosion was substantially eliminated.

A reactor lined with tantalum/tungsten alloy was used for making dimethyl carbonate as described above. The water content of the mixture in the reactor was maintained at a level of 6 to 10 weight percent. The reactor was run for 2, 4, and 6 months between inspections. Upon inspection no evidence of corrosion was found except where the water content was less than 4 weight percent.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents and other references are incorporated herein by reference in their entirety.

The invention claimed is:

1. A method of making a dialkyl carbonate comprising: reacting, in the presence of a reactor component comprising tantalum or a tantalum alloy, an alkanol, oxygen, and carbon monoxide in the presence of a catalyst comprising copper wherein the reaction occurs in a mixture comprising a liquid phase and flirt her wherein the liquid phase comprises about 4 to about 12 weight percent water based on the total weight of the liquid phase.

2. The method of claim 1 wherein the dialkyl carbonate is present in an amount of about 38 weight percent to about 52 weight percent, based on the total weight of the liquid phase.

3. The method of claim 1 wherein the alkanol is a $C_1$ to $C_4$ alkanol.

4. The method of claim 1 wherein the amount of water is 5 to 8 weight percent based on the total weight of the liquid phase.

5. The method of claim 1 wherein the catalyst is copper chloride.

6. The method of claim 1, wherein the reactor component comprises a tantalum/tungsten alloy.

7. The method of claim 1, wherein the repassivation potential of the tantalum or tantalum alloy in the liquid phase minus the corrosion potential of the liquid phase) is greater than 0.

8. A method of making a dialkyl carbonate comprising: reacting, in the presence of a reactor component comprising tantalum or a tantalum alloy, methanol, oxygen, and carbon monoxide, in the presence of a catalyst comprising copper wherein the reaction occurs in a mixture comprising a liquid phase and further wherein the liquid phase comprises about 4 to about 12 weight percent water based on the total weight of the liquid phase.

* * * * *

UNITED STATES PATENT AND TRADEMARK OFFICE
CERTIFICATE OF CORRECTION

PATENT NO. : 7,622,602 B2  
APPLICATION NO. : 11/248390  
DATED : November 24, 2009  
INVENTOR(S) : Ramgopal et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 940 days.

Signed and Sealed this

Fourteenth Day of December, 2010

David J. Kappos  
*Director of the United States Patent and Trademark Office*